(12) United States Patent
Guo et al.

(10) Patent No.: US 10,751,188 B2
(45) Date of Patent: Aug. 25, 2020

(54) SACRAL PROSTHESIS

(71) Applicant: Beijing AK Medical Co., Ltd., Beijing (CN)

(72) Inventors: Wei Guo, Beijing (CN); Caimei Wang, Beijing (CN); Tao Ji, Beijing (CN)

(73) Assignee: Beijing AK Medical Co., Ltd., Beijing (CN)

( * ) Notice: Subject to any disclaimer, the term of this patent is extended or adjusted under 35 U.S.C. 154(b) by 0 days.

(21) Appl. No.: 16/315,925

(22) PCT Filed: Jul. 8, 2016

(86) PCT No.: PCT/CN2016/089486
§ 371 (c)(1),
(2) Date: Jan. 7, 2019

(87) PCT Pub. No.: WO2018/006428
PCT Pub. Date: Jan. 11, 2018

(65) Prior Publication Data
US 2019/0298527 A1  Oct. 3, 2019

(51) Int. Cl.
*A61F 2/30* (2006.01)
*A61B 17/70* (2006.01)
(Continued)

(52) U.S. Cl.
CPC ...... *A61F 2/30988* (2013.01); *A61B 17/7011* (2013.01); *A61B 17/7032* (2013.01);
(Continued)

(58) Field of Classification Search
CPC ............... A61F 2/30988; A61F 2/28; A61F 2002/30001; A61F 2002/30011;
(Continued)

(56) References Cited

U.S. PATENT DOCUMENTS 4,773,402 A    9/1988  Asher et al.
5,545,164 A *  8/1996  Howland ........... A61B 17/7041
                                                      606/250
(Continued)

FOREIGN PATENT DOCUMENTS

CN    101011300 A    8/2007
CN    101547664 A    9/2009
(Continued)

OTHER PUBLICATIONS

International Search Report, in Chinese, translation of Search Report thereof, from counterpart PCT/CN2016/089486 dated Apr. 12, 2017, 6 pp.

(Continued)

*Primary Examiner* — Eduardo C Robert
*Assistant Examiner* — David C Comstock
(74) *Attorney, Agent, or Firm* — Shumaker & Sieffert, P.A.

(57) ABSTRACT

The present disclosure provides a sacral prosthesis, comprising: a prosthesis main body, the prosthesis main body including two first prosthesis bodies and a second prosthesis body connected between the two first prosthesis bodies the two first prosthesis bodies and the second prosthesis body being of an integrally prototyped structure, a second end of each of the first prosthesis bodies being contacted and matched with an ilium, and a top of the second prosthesis body being contacted and matched with a lumbar vertebral body; and a screw-rod structure, the screw-rod structure including a connecting seat and a rod body, the connecting seat being connected with the prosthesis main body, and the rod body being fixed on the connecting seat. The technical solutions of the present disclosure can effectively solve the problems of unreliable supporting and easy fatigue break of the screw-rod system in the related technology.

7 Claims, 3 Drawing Sheets

(51) Int. Cl.
*A61B 17/80* (2006.01)
*A61F 2/28* (2006.01)
*A61B 17/00* (2006.01)
*A61B 17/56* (2006.01)
*A61B 34/10* (2016.01)
*A61F 2/44* (2006.01)

(52) U.S. Cl.
CPC ...... *A61B 17/7037* (2013.01); *A61B 17/7055* (2013.01); *A61B 17/8061* (2013.01); *A61F 2/28* (2013.01); *A61B 2017/00004* (2013.01); *A61B 2017/00526* (2013.01); *A61B 2017/568* (2013.01); *A61B 2034/108* (2016.02); *A61F 2002/30001* (2013.01); *A61F 2002/30011* (2013.01); *A61F 2002/3092* (2013.01); *A61F 2002/3093* (2013.01); *A61F 2002/30507* (2013.01); *A61F 2002/30622* (2013.01); *A61F 2002/30738* (2013.01); *A61F 2002/30962* (2013.01); *A61F 2002/30985* (2013.01); *A61F 2002/30995* (2013.01); *A61F 2002/4495* (2013.01); *A61F 2220/0025* (2013.01)

(58) Field of Classification Search
CPC .. A61F 2002/30507; A61F 2002/30622; A61F 2002/30738; A61F 2002/3092; A61F 2002/3093; A61F 2002/30962; A61F 2002/30985; A61F 2002/30995; A61F 2002/4495; A61F 2220/0025; A61B 17/7011; A61B 17/7032; A61B 17/7037; A61B 17/7055; A61B 17/8061; A61B 2034/108; A61B 2017/00004; A61B 2017/00526; A61B 2017/568; A61B 17/8066
USPC ....... 606/246, 250, 253, 264, 266, 267, 268, 606/270, 280, 297, 298, 303, 319, 328
See application file for complete search history.

(56) References Cited

U.S. PATENT DOCUMENTS

| | | | | |
|---|---|---|---|---|
| 5,593,407 | A * | 1/1997 | Reis | A61B 17/7055 606/261 |
| 7,837,711 | B2 * | 11/2010 | Bruneau | A61B 17/7055 606/246 |
| 7,850,732 | B2 * | 12/2010 | Heinz | A61B 17/7055 623/17.11 |
| 8,801,757 | B2 * | 8/2014 | Abdou | A61B 17/7032 606/248 |
| 2007/0299445 | A1 * | 12/2007 | Shadduck | A61B 17/7011 606/86 A |
| 2012/0296428 | A1 * | 11/2012 | Donner | A61B 17/1739 623/17.11 |
| 2013/0304128 | A1 * | 11/2013 | Lange | A61B 17/705 606/264 |
| 2016/0302941 | A1 * | 10/2016 | Reiley | A61F 2/447 |
| 2017/0020572 | A1 * | 1/2017 | Hynes | A61B 17/7032 |

FOREIGN PATENT DOCUMENTS

| | | |
|---|---|---|
| CN | 101588764 A | 11/2009 |
| CN | 102293681 A | 12/2011 |
| CN | 104546228 A | 4/2015 |
| CN | 105342728 A | 2/2016 |
| CN | 106037993 A | 10/2016 |
| RU | 2585733 C1 | 6/2016 |

OTHER PUBLICATIONS

Communication and Supplemental European Search Report dated Sep. 5, 2019 for corresponding European Application No. 16907932. 4, 8 pgs.

\* cited by examiner

SACRAL PROSTHESIS

This application is a national stage entry under 35 U.S.C. § 371 of International Application No. PCT/CN2016/089486, filed Jul. 8, 2016. The entire contents of International Application No. PCT/CN2016/089486 is incorporated herein by reference.

TECHNICAL FIELD

The present disclosure relates to the field of medical devices, and more particularly, to a sacral prosthesis.

BACKGROUND

Sacrum is an important bone structure through which a human trunk is connected with limbs. An upward side of the sacrum is formed into a lumbosacral joint with a lumbar vertebra and two sides are formed into a sacroiliac joint with a pelvis. The sacrum is provided with important sacral nerves inside and the sacroiliac joint is also a unique structure for connecting axial bones and lower limb bones. As a result, this site has a great impact on nerve functions and structure stability after excision. For patients suffering from sacral tumors, a combination of a radiotherapy, a chemotherapy and tumor excision is a first choice for most sacral tumors. However, the sacral tumors have the characteristics that the early symptoms are few and when being found, most are huge, so for the sacral tumors, the excision extension is relatively large in an operation; and meanwhile, it seriously damages the local stability, and after the excision, the recovery of stress conduction and the reconstruction of stability at a lumbosacral portion are directly associated with postoperative functions and life quality of the patients. To recover the lumbosacral portion, three most important structures are a lumbar lordosis, a posterior pelvic ring and an anterior vertebral column. Particularly for the patients who receive a total sacrectomy, a bone defect will cause that the human trunk and pelvis are interrupted and the patients after the operation have the problems, for example, they possibly cannot stand and walk, and cannot look after themselves. If the sacrum is not effectively reconstructed, serious subsidence of the lumbar vertebra and lumbosacral nerve stretch may occur after the operation. The above-mentioned reconstruction after the sacrectomy is a big difficult problem in the bone tumor field internationally. Currently, there are multiple sacral tumor excision and reconstruction operations, among which structural bone grafting reconstruction is the most common. The structural bone grafting reconstruction is mainly classified into two categories. One is the "church type" reconstruction, which refers to directly support an inferior lumbar vertebra onto iliums by means of an iliac screw and a screw-rod system. The above structural bone grafting reconstruction can achieve the bearing effect in a short time, but from long-term follow-up observation, the screw rod is broken or loosed easily, the bone is damaged, and the patients are trapped in the state that they cannot stand and walk and cannot look after themselves and must receive a fixation operation again. The other is to reconstruct via an iliac rod, which refers to connect iliums at the two sides by means of a bone graft or an implant, recover the posterior pelvic ring and connect with horizontal structures such as metal rod or bone graft by means of the screw-rod system, thereby reconstructing the stress conduction from the lumbar vertebra to the iliums. For the above structural bone grafting reconstruction, the early stability needs to be provided by a metal implant, but the long-term stability requires bony fusion. In this sense, biologic reconstruction is of great importance to the long-term stability of the lumbosacral portion. From the biomechanical point of view, as a torque is relatively long after the lumbar vertebra and the pelvis are fixed, the lumbosacral portion will bear relatively high stress and shear force. Moreover, the above reconstruction methods cannot implement the complete fusion of the lumbar vertebra and the pelvis, resulting in that the stress is mainly focused on the metal implant. In a long run, the metal implant will be broken due to fatigue, and thus, it loses the fixation effect and is pulled. Although the pulling of the metal implant can be reduced by applying methods such as bone graft, hydroxyapatite, bone cement and long screw, the problem of the fatigue break of the metal implant still hasn't been solved; and thus, it is difficult to implement the effective reconstruction.

SUMMARY

Some embodiments of the present disclosure provide a sacral prosthesis, so as to solve the problems of unreliable supporting and easy fatigue break of a screw-rod system in the related technology.

To this end, an embodiment of the present disclosure provides a sacral prosthesis, including: a prosthesis main body, the prosthesis main body including two first prosthesis bodies and a second prosthesis body connected between the two first prosthesis bodies, a first end of each of the first prosthesis bodies being connected with the second prosthesis body, the two first prosthesis bodies and the second prosthesis body being of an integrally prototyped structure, a second end of each of the first prosthesis bodies being extended along a direction far away from the second prosthesis body, and being contacted and matched with an ilium, and a top of the second prosthesis body being contacted and matched with a lumbar vertebral body; and a screw-rod structure, the screw-rod structure including a connecting seat and a rod body, the connecting seat being connected with the prosthesis main body, and the rod body being fixed on the connecting seat.

In an exemplary embodiment, a first screw hole is formed in at least one of the first prosthesis bodies; the first screw hole is conical hole; a first screw seat is arranged in the first screw hole; and the first screw seat is provided with a spherical inner surface; and/or a second screw hole is formed in the second prosthesis body; the second screw hole is a conical hole; a second screw seat is arranged in the second screw hole; and the second screw seat is provided with a spherical inner surface.

In an exemplary embodiment, the connecting seat includes: a connecting screw, one end of the connecting screw being connected with the prosthesis main body, and the other end of the connecting screw being provided with a spherical screw head; and a rod body fixing portion configured to fix the rod body, one end of the rod body fixing portion being provided with a spherical hole matched with the spherical screw head so that the rod body fixing portion is rotatably arranged on the connecting screw.

In an exemplary embodiment, rod body fixing portion includes a U-shaped support and a fixing cap; and the rod body is arranged between the U-shaped support and the fixing cap in a clamping manner.

In an exemplary embodiment, the prosthesis main body is of a hollow truss structure; and the prosthesis main body is prototyped by 3D printing.

In an exemplary embodiment, the second end of each of the first prosthesis bodies and/or the top of the second prosthesis body are/is provided with a porous structure.

In an exemplary embodiment, the second end of each of the first prosthesis bodies and/or the top of the second prosthesis body are/is provided with a needlelike bump.

In an exemplary embodiment, a surface, facing toward a pelvic cavity, of the prosthesis main body is a smooth surface.

In an exemplary embodiment, an anti-dropping mechanism is arranged on the prosthesis main body; the anti-dropping mechanism is arranged between the prosthesis main body and the connecting seat in a clamping manner; and the anti-dropping mechanism includes a first anti-dropping tentacle matched with a screw accommodated in the first screw hole.

In an exemplary embodiment, the anti-dropping mechanism further includes an anti-dropping main body; the anti-dropping main body is arranged between the prosthesis main body and the connecting seat in a clamping manner; the anti-dropping mechanism further includes a second anti-dropping tentacle; the first anti-dropping tentacle and the second anti-dropping tentacle are connected with the anti-dropping main body and are extended outward; and a limiting sleeve matched with the rod body are arranged on the second anti-dropping tentacle.

By applying the technical solutions of the present disclosure, the sacral prosthesis includes the prosthesis main body, the prosthesis main body includes the two first prosthesis bodies and the second prosthesis body connected between the two first prosthesis bodies, the first end of each of the first prosthesis bodies is connected with the second prosthesis body, the second end of each of the first prosthesis bodies is extended along the direction far away from the second prosthesis body and is contacted and matched with the ilium, and the top of the second prosthesis body is contacted and matched with the lumbar vertebral body. An outline of the prosthesis main body is formed into an "inverted V-shaped" structure, so the good mechanical property is obtained, and the internal force distribution of the structure is improved. Under the condition of bearing a relatively high stress and a relatively high shear force, the rigidity of the sacral prosthesis can be maintained, so that a bone is not damaged easily. Therefore, the above-mentioned structure solves the problem that the bone is easily damaged due to the unreliable supporting and the easy fatigue break of the screw-rod system in the related technology. And in addition, by applying the technical solutions of the present disclosure, the screw-rod structure includes the connecting seat and the rod body, the connecting seat is connected with the prosthesis main body, and the rod body is fixed on the connecting seat. The above structure reinforces the fixing between the prosthesis main body and the lumbar vertebral body and increases the stability of the lumbar vertebral body, thereby preventing the subsidence of a lumbar vertebra portion.

BRIEF DESCRIPTION OF THE DRAWINGS

The accompanying drawings are described here to provide further understanding of the present disclosure, and form a part of the present disclosure. The schematic embodiments and description of the present disclosure are adopted to explain the present disclosure, and do not form improper limits to the present disclosure.

The above accompanying drawings include the following labels:

1. an ilium; 2. a lumbar vertebral body; 11. a first prosthesis body; 111. a first screw hole; 12. a second prosthesis body; 121. a second screw hole; 21. a connecting seat; 211. a connecting screw; 2111. a spherical screw head; 212. a rod body fixing portion; 2121. a U-shaped support; 2122. a fixing cap; 22. a connecting seat; 221. a connecting screw; 2211. a spherical screw head; 222. a rod body fixing portion; 2221. a U-shaped support; 2222. a fixing cap; 23. a rod body; 30. an anti-dropping mechanism; 31. a first anti-dropping tentacle; 32. an anti-dropping main body; 33. a second anti-dropping tentacle; 34. a limiting sleeve.

DETAILED DESCRIPTION

It is to be noted that the embodiments of the present application and the characteristics of the embodiments may be combined with each other if there is no conflict. The present disclosure is described below with reference to the drawings and embodiments in detail.

Figure 1:
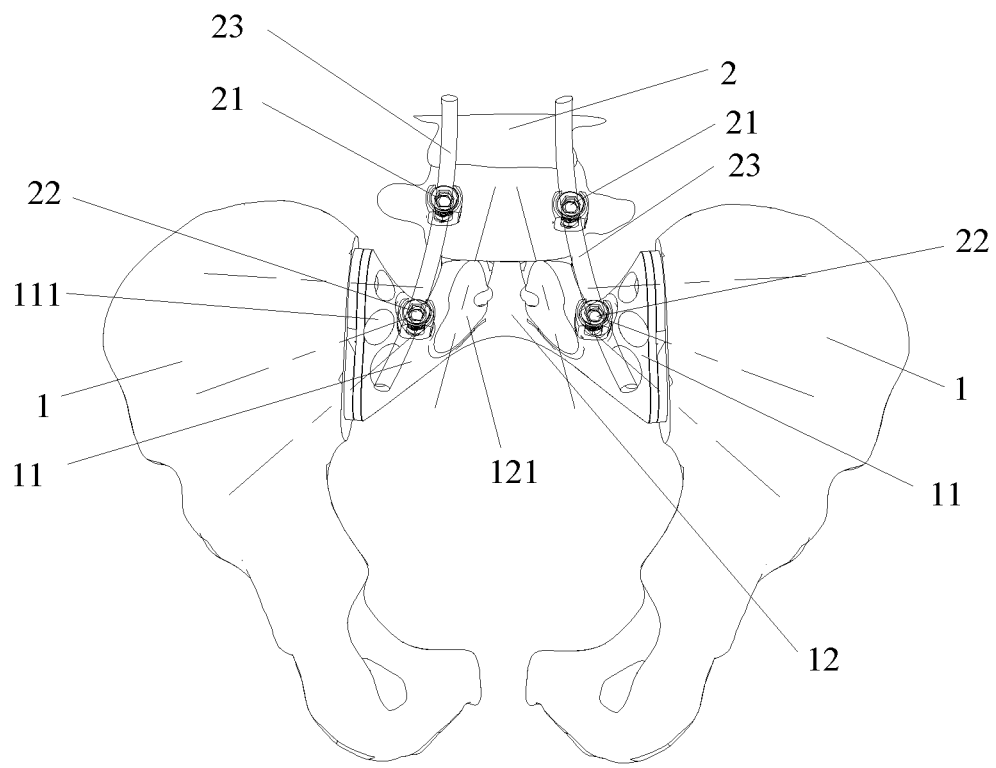
FIG. 1 depicts an assembly diagram according to an embodiment of a sacral prosthesis of the present disclosure.

As shown in FIG. 1, the sacral prosthesis of the embodiment includes a prosthesis main body and a plurality of screw-rod structures, wherein the prosthesis main body includes two first prosthesis bodies 11 and a second prosthesis body 12 connected between the two first prosthesis bodies 11; a first end of each of the first prosthesis bodies 11 is connected with the second prosthesis body 12; the two first prosthesis bodies 11 and the second prosthesis body 12 are of an integrally prototyped structure; a second end of each of the first prosthesis bodies 11 is extended along a direction far away from the second prosthesis body 12, and is contacted and matched with an ilium 1; a top of the second prosthesis body 12 is contacted and matched with a lumbar vertebral body 2; each of the screw-rod structures includes connecting seat 22 a rod body 23; the connecting seat 22 are connected with the prosthesis main body; and the rod body 23 are fixed on the connecting seat 22.

By applying the technical solution of the embodiment, the sacral prosthesis includes the prosthesis main body, the prosthesis main body includes the two first prosthesis bodies 11 and the second prosthesis body 12 connected between the two first prosthesis bodies 11, the first end of each of the first prosthesis bodies 11 is connected with the second prosthesis body 12, the second end of each of the first prosthesis bodies 11 is extended along the direction far away from the second prosthesis body 12 and is contacted and matched with the ilium 1, and the top of the second prosthesis body 12 is contacted and matched with the lumbar vertebral body 2. The prosthesis main body is formed into an "inverted V-shaped" structure, so the good mechanical property is obtained, and the internal force distribution of the structure is improved. Under the condition of bearing a relatively high stress and a relatively high shear force, the rigidity of the sacral prosthesis can be maintained, so that a bone is not damaged easily. Therefore, the above-mentioned structure solves the problem that the bone is easily damaged due to the unreliable supporting and the easy fatigue break of the screw-rod system in the related technology. And in addition, by applying the technical solutions of the embodiment, the screw-rod structures include the connecting seat 22 and the rod body 23, the connecting seat 22 are connected with the prosthesis main body, and the rod body 23 is fixed on the connecting seat 22. The above structure reinforces the fixing between the prosthesis main body and the lumbar vertebral body 2 and increases the stability of the lumbar vertebral body 2, thereby preventing the subsidence of a lumbar vertebra portion.

Figure 3:
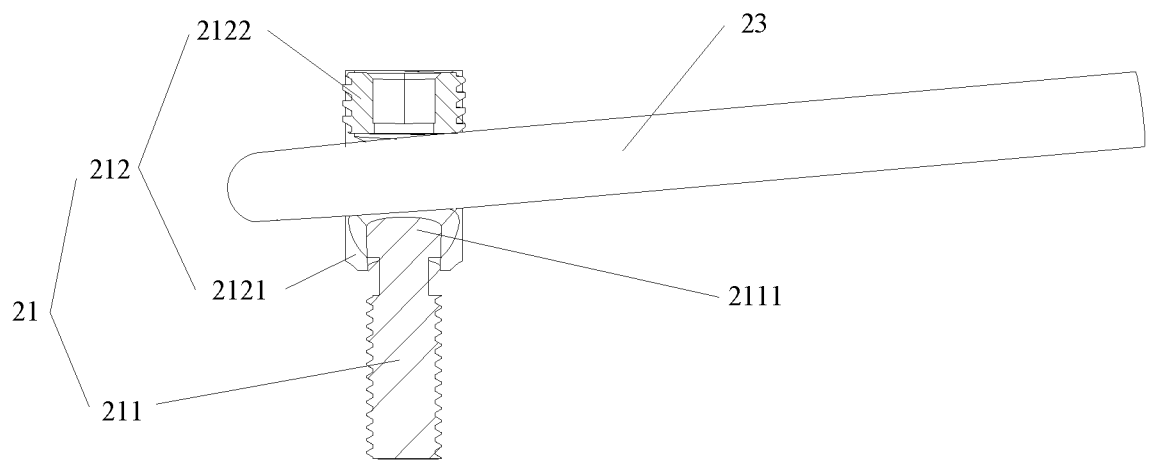
FIG. 3 depicts a schematic diagram of a longitudinal section structure of the connecting seat in FIG. 2.

As shown in FIG. 3, in the embodiment, each of the screw-rod structures further includes connecting seat 21; the connecting seat 21 is connected with the lumbar vertebral body; the rod body 23 is fixed on the connecting seat 21; the connecting seat 21 includes: a connecting screw 211, one end of the connecting screw 211 being connected with the lumbar vertebral body 2, and the other end of the connecting screw 211 being provided with a spherical screw head 2111; and a rod body fixing portion 212 configured to fix the rod body 23, one end of the rod body fixing portion 212 being provided with a spherical hole matched with the spherical screw head 2111. With the above structure, the rod body fixing portion 212 can be rotatably arranged on the connecting screw 211. In this way, a doctor may adjust positions of the rod body 23 according to an actual demand, and thus, an installation position is more accurate, and an installation process is simpler.

Figure 2:
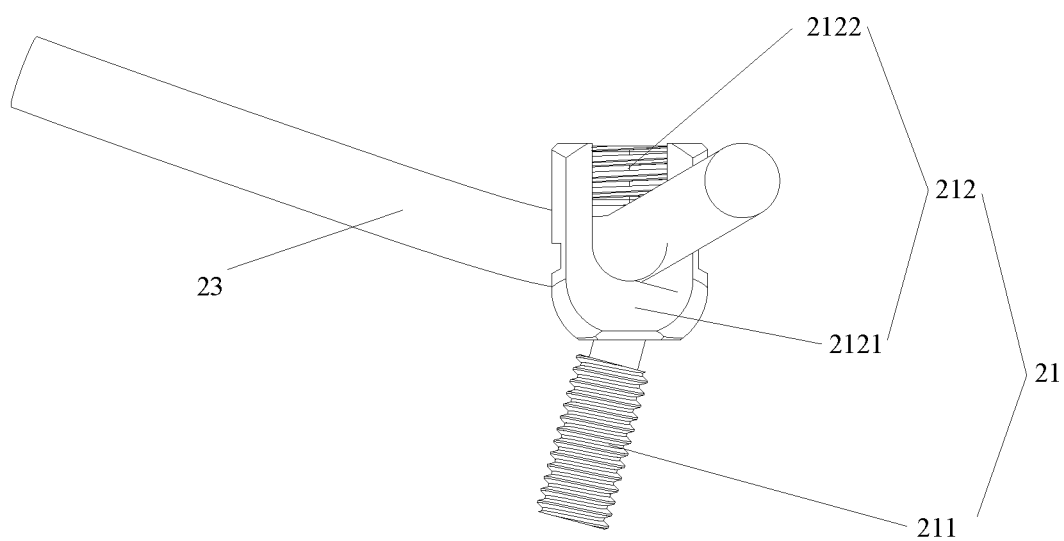
FIG. 2 depicts a three-dimensional structure schematic diagram of a connecting seat of the sacral prosthesis in FIG. 1.

As shown in FIG. 2, in the embodiment, the rod body fixing portion 212 includes a U-shaped support 2121 and a fixing cap 2122; and the rod body 23 is arranged between the U-shaped support 2121 and the fixing cap 2122 in a clamping manner. Specifically, an installation space is formed in U-shaped inner wall of the U-shaped support 2121, and the rod body 23 is inserted into the installation space. An upper part of the U-shaped inner wall of the U-shaped support 2121 is provided with an inner screw thread, and the fixing cap 2122 is provided with an outer screw thread matched with the inner screw thread of the U-shaped support 2121. When the rod body 23 is installed, it is necessary to first enable the rod body 23 to go through the installation space and then screw the fixing cap 2122 to the U-shaped support 2121. Therefore, the above structure is simple, and convenient to install.

Figure 5:
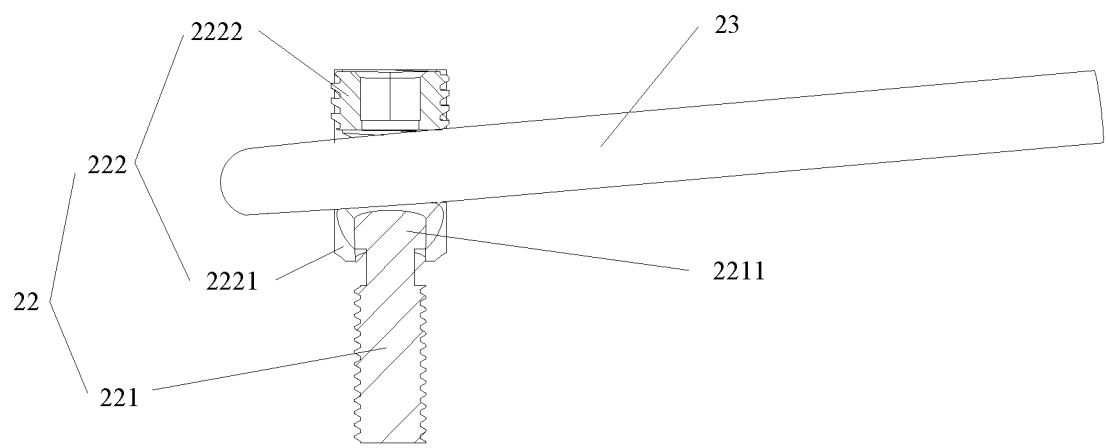
FIG. 5 depicts a schematic diagram of a longitudinal section structure of the another connecting seat in FIG. 4.

As shown in FIG. 5, in the embodiment, each of the screw-rod structures further includes connecting seat 22; the connecting seat 22 is connected with the prosthesis main body; the connecting seat 22 includes: a connecting screw 221, one end of the connecting screw 221 being connected with the prosthesis main body, and the other end of the connecting screw 221 being provided with a spherical screw head 2211; and a rod body fixing portion 222 configured to fix the rod body 23, one end of the rod body fixing portion 222 being provided with a spherical hole matched with the spherical screw head 2211. With the above structure, the rod body fixing portion 222 can be rotatably arranged on the connecting screw 221. In this way, a doctor may adjust positions of the rod body 23 according to an actual demand, and thus, an installation position is more accurate, and an installation process is simpler.

Figure 4:
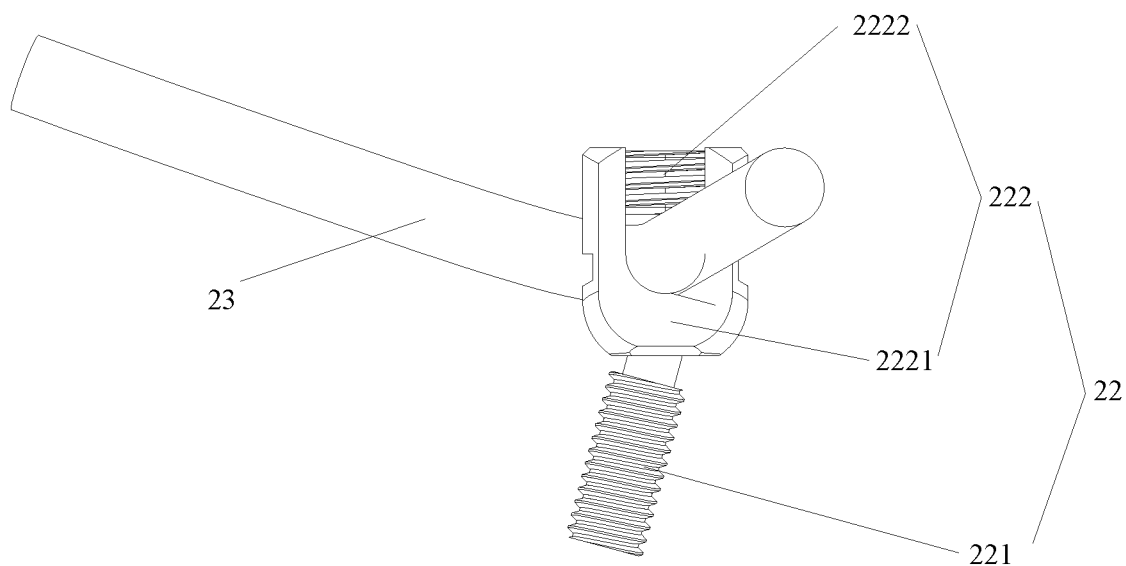
FIG. 4 depicts a three-dimensional structure schematic diagram of another connecting seat of the sacral prosthesis in FIG. 1.

As shown in FIG. 4, in the embodiment, the rod body fixing portion 222 includes a U-shaped support 2221 and a fixing cap 2222; and the rod body 23 is arranged between the U-shaped support 2221 and the fixing cap 2222 in a clamping manner. Specifically, an installation space is formed in U-shaped inner wall of the U-shaped support 2221, and the rod body 23 is inserted into the installation space. An upper part of the U-shaped inner wall of the U-shaped support 2221 is provided with an inner screw thread, and the fixing cap 2222 is provided with an outer screw thread matched with the inner screw thread of the U-shaped support 2221. When the rod body 23 is installed, it is necessary to first enable the rod body 23 to go through the installation space and then screw the fixing cap 2222 to the U-shaped support 2221. Therefore, the above structure is simple, and convenient to install.

In the embodiment, the prosthesis main body is of a hollow truss structure. On one hand, the truss structure can greatly reduce the weight of the prosthesis main body and improves the material utilization rate, and simultaneously further can guarantee the strength and the rigidity of the prosthesis main body. On the other hand, with the adoption of the above structure, the prosthesis main body is closer to an adjacent skeleton, so that the bony fusion effect is better. Because anatomic reconstruction after the pelvic tumor excision needs to satisfy the accurate and complex requirements, and even further needs to satisfy the disposable and tailor-made requirements, the prosthesis main body is prototyped by means of 3D printing in the embodiment. And the above process intrinsically has the characteristics of being accurate, being capable of manufacturing a complex part and being capable of personally customized.

It is to be noted that a Three-Dimensional (3D) printing rapid prototyping technology is a brand-new manufacturing technology based on a material stacking method, is different from the traditional removed material processing technology, and is also referred to as Additive Manufacturing (AM). The 3D printing technology is to stack layers of a material into an entity via a rapid prototyping machine by employing 3D CAD data. It is named because though different types of rapid prototyping systems have different prototyping principles and system characteristics depending on different prototyping materials used, their basic principles are the same and are to "manufacture in layers and overlap one by one", just like a "3D printer". With the rapid development of cutting-edge technologies such as manufacturing technology, digital modeling technology, numerical control technology, information technology, material science technology, chemical and biological technologies as well as the multidisciplinary close cooperation, the development of the 3D printing technology has become one of the most popular new technologies at present. The 3D printing will have a broad application prospect in the orthopedics field in future because its characteristics meet special requirements of the orthopedics. On one hand, bone tissues are a typical example of a complex structure, and it is very hard for the existing bionic technology to copy their special 3D forms and physiological functions. However, the 3D printing is just suitable for the rapid manufacturing of the complex structure and can obtain an approximately ideal bone repair material. And on the other hand, human bodies have a highly individual specificity, the traditional medical products produced in large scale and in batches cannot meet the personalized requirement and the former personalized and customized products produced by means of a manufacturing process such as mould have a high cost and a long period. Following the widespread application of a digital imaging technology in the medical field, the skeleton is an organ easiest to obtain an accurate digital image; and by combining with the skeleton and the 3D printing, the personalized medical products may be produced accurately and rapidly at a low cost. Therefore, by virtue of the 3D printing technology, an implant product with any form and an ideal biomechanical strength can be casted in a short time, making the development of personalized and customized bone implant products become true.

As shown in FIG. 1, in the embodiment, a plurality of first screw holes 111 are formed in each of the first prosthesis bodies 11; each of the first screw holes 111 is conical hole; a plurality of first screw seats are respectively arranged in the first screw holes 111; and each of the first screw seats is provided with a spherical inner surface. When the doctor needs to fix the prosthesis main body onto the ilium 1 via screws, the screws are respectively penetrated into the first screw holes 111 first. Since each of the first screw holes 111 is conical hole, head portion of each of the screws is spherical head and each of the first screw seats is provided with the spherical inner surface matched with the spherical head, the screws can be rotated in a certain range, and the doctor may choose nailing directions of the screws in terms of a practical condition. With the above structure, the doctor can choose screw fixing positions according to the practical condition, so that the fixing effect between the prosthesis main body and the ilium 1 is better. It is to be noted that dotted lines in FIG. 1 are the nailing directions of the screws. Likewise, a second screw hole 121 is formed in the second prosthesis body 12, the second screw hole 121 is a conical hole, a second screw seat is arranged in the second screw hole 121 and the second screw seat is provided with a spherical inner surface. With the above structure, the doctor can choose a screw fixing position according to the practical condition, so that the fixing effect between the prosthesis main body and the lumbar vertebral body 2 is better.

In the embodiment, the second end of each of the first prosthesis bodies 11 is provided with a first porous structure (not shown in Figure). The above structure can rapidly promote the generation of bone cells and is easily integrated with the bone (ilium), thereby achieving the medium-long term fixing effect. Compared with the traditional operation mode, it has the characteristics of high strength, high stability and strong bone integration capability.

In the embodiment, the top of the second prosthesis body 12 is provided with a second porous structure (not shown in Figure). The above structure can rapidly promote the generation of bone cells and is easily integrated with the bone (lumbar vertebral body), thereby achieving the medium-long term fixing effect. Compared with the traditional operation mode, it has the characteristics of high strength, high stability and strong bone integration capability.

In the embodiment, the second end of each of the first prosthesis bodies 11 is provided with a first needlelike bump (not shown in Figure). The needlelike bump has the effects of cutting and anchoring, so that the ilium is fixed with the second ends of the first prosthesis bodies 11 together.

In the embodiment, the top of the second prosthesis body 12 is provided with a second needlelike bump (not shown in Figure). The needlelike bump has the effects of cutting and anchoring, so that the lumbar vertebral body is fixed with the top of the second prosthesis body 12 together.

In the embodiment, a surface, facing toward a pelvic cavity, of the prosthesis main body is a smooth surface (not shown in Figure). The above structure can reduce a bruise of the sacral prosthesis to soft tissues such as intestinal tract in the pelvic cavity, thereby taking a certain protective effect to the soft tissues such as intestinal tract in the pelvic cavity of the patient.

Figure 6:
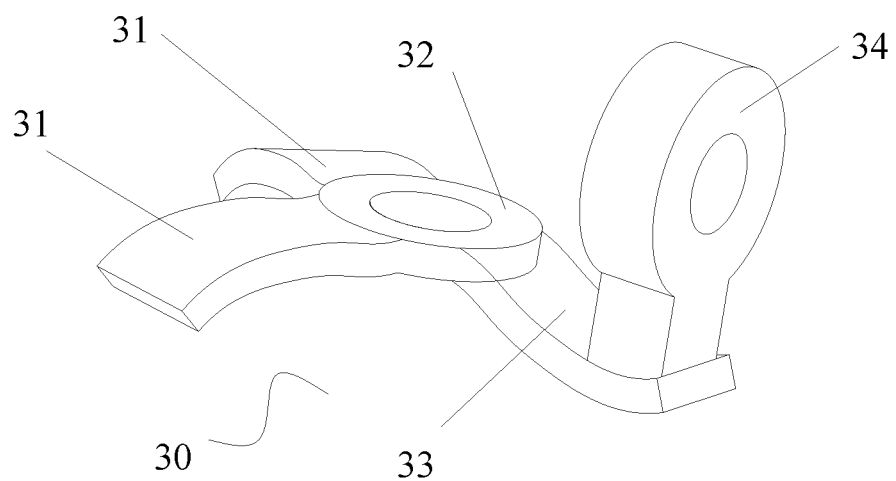
FIG. 6 depicts a three-dimensional structure schematic diagram of an anti-dropping mechanism of the sacral prosthesis in FIG. 1.

As shown in FIG. 6, in the embodiment, anti-dropping mechanism 30 is arranged on the prosthesis main body; the anti-dropping mechanism 30 is arranged between the prosthesis main body and the connecting seat 22 in a clamping manner; and the anti-dropping mechanism 30 includes a plurality of first anti-dropping tentacles 31 matched with the screws accommodated in the screw holes 111. When the connecting seat 22 is screwed tightly in use, the first anti-dropping tentacles 31 are propped against the screws accommodated in the screw holes 111. The tighter the connecting screw 221 of the connecting seat 22 is, the greater a force that the first anti-dropping tentacles 31 are propped against the screws is. Therefore, the above structure can prevent the screws from dropping out from the screw holes 111. In addition, it is common that the connecting screw 221 screwed to the bone is loosed in the related technology, so the anti-dropping mechanism 30 further can provide a pretightening force for the connecting seat 22 so as to prevent the looseness of the connecting seat 22.

As shown in FIG. 6, in the embodiment, the anti-dropping mechanism 30 further includes an anti-dropping main body 32; the anti-dropping main body 32 is arranged between the prosthesis main body and the connecting seat 22 in a clamping manner; the anti-dropping mechanism 30 further includes a second anti-dropping tentacle 33; the first anti-dropping tentacles 31 and the second anti-dropping tentacle 33 are connected with the anti-dropping main body 32 and are extended outward; and a limiting sleeve 34 matched with the rod body 23 is arranged on the second anti-dropping tentacle 33. Preferably, multiple first anti-dropping tentacle 31 matched with the screw hole 111 are provided. Because the first anti-dropping tentacles 31 are extended outward to the screw holes 111, and the anti-dropping main body 32 is arranged between the prosthesis main body and the connecting seat 22 in a clamping manner, the anti-dropping mechanism 30 is limited and cannot be rotated. And the limiting sleeve 34 is arranged on the second anti-dropping tentacle 33 and the limiting sleeve 34 is matched with the rod body 23, so the rod body 23 is also limited and cannot be rotated. Therefore, the above structure prevents the rotation of the rod body 23, thereby increasing the stability of the system.

Preferably, the anti-dropping mechanism 30 is leaf springs; a tail end of the second anti-dropping tentacle 33 of the leaf spring is tilted upward; and the a limiting sleeve 34 is arranged at the tail end of the second anti-dropping tentacle 33.

The above description is only preferred embodiments of the present disclosure and is not intended to limit the present disclosure. Persons in the art can make various modifications and changes of the present disclosure. Any modification, equivalent replacement, or improvement made within the spirit and principle of the present disclosure shall all fall within the protection scope of the present disclosure.

What is claimed is:
1. A sacral prosthesis, comprising:
a prosthesis main body, the prosthesis main body comprising two first prosthesis bodies and a second prosthesis body connected between the two first prosthesis bodies, a first end of each of the first prosthesis bodies being connected with the second prosthesis body, the two first prosthesis bodies and the second prosthesis body being of an integrally prototyped structure, a second end of each of the first prosthesis bodies being extended along a direction far away from the second prosthesis body, and being contacted and matched with an ilium, and a top of the second prosthesis body being contacted and matched with a lumbar vertebral body; and a screw-rod structure, the screw-rod structure comprising a connecting seat and a rod body, the connecting seat being connected with the prosthesis main body, and the rod body being fixed on the connecting seat;

wherein the sacral prostheses further comprises:
- a first screw seat arranged in a first screw hole formed in at least one of the first prosthesis bodies, the first screw hole being a conical hole and the first screw seat having a spherical inner surface; and/or
- a second screw seat arranged in a second screw hole formed in the second prosthesis body, the second screw hole being a conical hole and the second screw seat having a spherical inner surface, and wherein an anti-dropping mechanism is arranged on the prosthesis main body, the anti-dropping mechanism arranged between the prosthesis main body and the connecting seat in a clamping manner, wherein the anti-dropping mechanism comprises:
- a first anti-dropping tentacle matched with a screw accommodated in the screw hole; and
- an anti-dropping main body arranged between the prosthesis main body and the connecting seat in a clamping manner;
- a second anti-dropping tentacle, the first anti-dropping tentacle and the second anti-dropping tentacle being connected with the anti-dropping main body and extended outward; and
- a limiting sleeve matched with the rod body and arranged on the second anti-dropping tentacle.

2. The sacral prosthesis as claimed in claim 1, wherein the connecting seat comprises:
- a connecting screw, one end of the connecting screw being connected with the prosthesis main body, and the other end of the connecting screw being provided with a spherical screw head; and
- a rod body fixing portion configured to fix the rod body, one end of the rod body fixing portion being provided with a spherical hole matched with the spherical screw head so that the rod body fixing portion is rotatably arranged on the connecting screw.

3. The sacral prosthesis as claimed in claim 2, wherein rod body fixing portion comprises a U-shaped support and a fixing cap; and the rod body is arranged between the U-shaped support and the fixing cap in a clamping manner.

4. The sacral prosthesis as claimed in claim 1, wherein the prosthesis main body is of a hollow truss structure; and the prosthesis main body is prototyped by 3D printing.

5. The sacral prosthesis as claimed in claim 1, wherein the second end of each of the first prosthesis bodies and/or the top of the second prosthesis body are/is provided with a porous structure.

6. The sacral prosthesis as claimed in claim 1, wherein the second end of each of the first prosthesis bodies and/or the top of the second prosthesis body are/is provided with a needlelike bump.

7. The sacral prosthesis as claimed in claim 1, wherein a surface, facing toward a pelvic cavity, of the prosthesis main body is a smooth surface.

* * * * *